United States Patent
Grob

(10) Patent No.: US 11,224,465 B2
(45) Date of Patent: Jan. 18, 2022

(54) SURGICAL METHODS FOR THE TREATMENT OF SPINAL STENOSIS

(71) Applicant: SpineWelding AG, Schlieren (CH)

(72) Inventor: Dieter Grob, Erlenbach (CH)

(73) Assignee: SPINEWELDING AG, Schlieren (CH)

( * ) Notice: Subject to any disclaimer, the term of this patent is extended or adjusted under 35 U.S.C. 154(b) by 99 days.

(21) Appl. No.: 16/209,029

(22) Filed: Dec. 4, 2018

(65) Prior Publication Data

US 2020/0170676 A1 Jun. 4, 2020

(51) Int. Cl.
| | |
|---|---|
| *A61B 17/70* | (2006.01) |
| *A61B 17/04* | (2006.01) |
| *A61B 17/16* | (2006.01) |
| *A61B 17/86* | (2006.01) |
| *A61B 17/00* | (2006.01) |
| *A61B 17/02* | (2006.01) |

(52) U.S. Cl.
CPC ........ *A61B 17/707* (2013.01); *A61B 17/0401* (2013.01); *A61B 17/1671* (2013.01); *A61B 17/7067* (2013.01); *A61B 17/1659* (2013.01); *A61B 17/86* (2013.01); *A61B 2017/00469* (2013.01); *A61B 2017/0256* (2013.01)

(58) Field of Classification Search
CPC ................ A61B 17/0401; A61B 17/86; A61B 2017/042; A61B 17/1671; A61B 17/7067; A61B 17/707; A61B 2017/0448; A61B 2017/0459; A61B 2017/0446
USPC ......................................................... 606/232
See application file for complete search history.

(56) References Cited

U.S. PATENT DOCUMENTS

| | | | | |
|---|---|---|---|---|
| 6,045,551 | A * | 4/2000 | Bonutti | A61B 17/0401 606/215 |
| 8,926,664 | B1 * | 1/2015 | Millhouse | A61B 17/8866 606/246 |
| 9,737,337 | B2 * | 8/2017 | Ferree | A61B 17/7053 |
| 2004/0030341 | A1 * | 2/2004 | Aeschlimann | B29C 66/727 606/232 |
| 2004/0138683 | A1 * | 7/2004 | Shelton | A61B 17/0401 606/151 |
| 2006/0089646 | A1 * | 4/2006 | Bonutti | A61F 2/0811 606/279 |

(Continued)

FOREIGN PATENT DOCUMENTS

WO    2012/100358    8/2012

OTHER PUBLICATIONS

C.A. Bailey et al., "Biomechanical Evaluation of a New Composite Bioresorbable Screw", The Journal of Hand Surgery, Apr. 2006, vol. 31B, No. 2, pp. 208-212.

(Continued)

*Primary Examiner* — Eduardo C Robert
*Assistant Examiner* — Tara Rose E Carter
(74) *Attorney, Agent, or Firm* — Rankin, Hill & Clark LLP

(57) ABSTRACT

A method for the treatment of spinal stenosis that includes cutting off a muscle origin or insertion from a spinous process, cutting off the spinous process at the transition to the lamina arcus vertebrae, resecting at least a part of the lamina arcus vertebrae and thereby decompression of the spinal cord within the foramen vertebral, performing osteosynthesis of the spinous process and placing a suture anchor within the spinous process and reattaching the muscle origin or insertion to the spinous process.

12 Claims, 5 Drawing Sheets

(56) References Cited

U.S. PATENT DOCUMENTS

| | | | |
|---|---|---|---|
| 2007/0073293 A1* | 3/2007 | Martz | A61B 17/7062 |
| | | | 606/86 A |
| 2007/0191957 A1* | 8/2007 | Anderson | A61B 17/0401 |
| | | | 623/17.16 |
| 2008/0125779 A1* | 5/2008 | Ferree | A61B 17/7022 |
| | | | 606/246 |
| 2010/0082067 A1* | 4/2010 | Kondrashov | A61B 17/7064 |
| | | | 606/264 |
| 2011/0106083 A1* | 5/2011 | Voellmicke | A61B 17/7059 |
| | | | 606/70 |
| 2012/0078300 A1 | 3/2012 | Mayer et al. | |
| 2012/0158061 A1* | 6/2012 | Koch | A61F 2/4611 |
| | | | 606/248 |
| 2013/0274809 A1* | 10/2013 | Ferree | A61B 17/7022 |
| | | | 606/279 |

OTHER PUBLICATIONS

Liming Fang et al., "Processing and mechanical properties of HA/UHMWPE nanocomposites", Biomaterials (2006), vol. 27, pp. 3701-3707, Elsevier Ltd.

Xiao Huang et al., "Novel Porous Hydroxyapatite Prepared by Combining H2O2 Foaming with PU Sponge and Modified with PLGA and Bioactive Glass", Journal of Biomaterials Applications, Apr. 23, 2007, vol. 21, pp. 351-374, http:/jba.sagepub.com/.

S.M. Rea et al., "Bioactivity of ceramic-polymer composites with varied composition and surface topography", Journal of Materials Science; Materials in Medicine, (2004), vol. 15, pp. 997-1005, Cambridge, UK.

International Search Report dated May 19, 2020, Application No. PCT/EP2019/083732, 7 pages.

\* cited by examiner

SURGICAL METHODS FOR THE TREATMENT OF SPINAL STENOSIS

BACKGROUND OF THE INVENTION

Field of the Invention

The invention is in the field of surgical procedures and concerns in particular methods for spinal surgery. The inventive methods refers mainly to the treatment of spinal stenosis, which may be caused by spinal osteoarthritis or degenerative disc disease.

Description of Related Art

Spinal stenosis is the narrowing of the spinal column in one or more areas, which may lead to the compression of the spinal cord and spinal nerves. Spinal decompression surgery is a general term that refers to various procedures intended to relieve symptoms caused by pressure, or compression, on the spinal cord and/or nerve roots. Bulging or collapsed disks, thickened joints, loosened ligaments, and bony growths can narrow the spinal canal and the spinal nerve openings (foramen), causing irritation. Spinal stenosis can occur in the cervical, lumbar or thoracic region of the spine, and often results in chronic back and neck pain. This disorder usually involves the narrowing of one or more of the following: (1) the canal in the center of the vertebral column through which the spinal cord and nerve roots run, (2) the canals at the base or roots of nerves branching out from the spinal cord, or (3) the openings between vertebrae through which nerves leave the spine and go to other parts of the body.

Spinal stenosis treatment options range from conservative to the more aggressive and depends on the severity of the symptoms. In the event that the symptoms have reached a level where the condition is debilitating and non-surgical treatments have failed to alleviate pain, surgery for spinal stenosis treatment may be required for long-term relief. Since spinal stenosis is at its core a condition that compresses the spinal canal, any surgery for spinal stenosis would have to relieve that compression in order to alleviate the symptoms associated with it. The primary goal of any decompression surgery of the spine is to provide additional space for the constricted spinal cord, nerve roots or nerves to pass through. Once this space has been opened up, the pain, inflammation, and numbness associated with spinal stenosis should subside. A decompression surgery for spinal stenosis is performed in order to return any lost mobility or motor skills associated with the condition as well.

Laminectomy or laminotomy are surgical methods to treat spinal stenosis. These procedures involve removing a small part of the bony arches of the spinal canal, called the lamina. During a laminotomy, just a section of the lamina is removed. During a laminectomy, the entire lamina is removed. Removing the lamina enlarges the spinal canal, thus relieving the pressure on compressed nerves. Lumbar fusion is frequently preformed in conjunction with laminectomy. Current fusion techniques increase the risk of spinal stenosis procedures. Various fusion techniques require the severing and/or removal of certain structural soft tissues (e.g. muscle attachments, ligaments) surrounding the spine.

Alternative methods are a foraminotomy or foraminectomy. Both procedures are performed to expand the openings for the nerve roots to exit the spinal cord by removing some bone and other tissue. A foraminectomy generally refers to a procedure that removes a large amount of bone and tissue. The above described techniques may be combined with osteophyte removal, involving to remove bony growths called osteophytes or bone spurs. Further corpectomy may be necessary. This is a method removing the body of a vertebra, as well as the disks.

A combination of techniques may be used; and in some cases, fusion of the vertebrae also is needed to stabilize the spine. Increasingly, surgeons are looking for improved methods of effecting less invasive treatments for spinal stenosis. The device must be able to be safely and consistently implanted without excess damage to the patient. The present invention is directed at overcoming, or at least improving upon, the disadvantages of the prior art.

SUMMARY OF THE INVENTION

It is accordingly an object of the present invention to provide method with which the above disadvantages could at least partially be overcome or alleviated and/or to provide a more useful alternative to the known methods of spinal decomression. In particular, it is an object to provide a novel method for laminectomy or laminotomy with less harm to autochthone back muscles. The newly developed methods in spine surgery are based on the use of suture anchors which allow to anchor a suture within a very short bone opening, so that the anchors may be located in structures allowing only little room for anchoring.

The methods of the present invention are especially suitable for the treatment of a spinal stenosis. A first aspect of the present invention refers to a method for the treatment of spinal stenosis including the following steps:

cutting off a muscle origin or insertion from a spinous process cutting off the spinous process at the transition to the lamina arcus vertebrae at least partial resection of the lamina arcus vertebrae and thereby decompression of the spinal cord within the foramen vertebral performing osteosynthesis of the spinous process and placing a suture anchor within the spinous process and reattaching the muscle origin or insertion to the spinous process.

The method according to the first aspect of the invention is suitable to treat nearly all vertebrae. Thus, the first aspect of the invention includes methods, wherein the spinal stenosis is a cervical spinal canal stenosis, thoracic spinal canal stenosis, lumbar spinal canal stenosis or wide spinal canal stenosis.

As any common surgical method, the methods of the invention may further include the step of surgical incision (cut made through the skin to facilitate the following surgical method or procedure) or multiple incisions. The location and size of the incision depends on the vertebrae to be treated. One possibility is that the back is approached through a 5 to 10 centimeter long incision in the midline of the back. The step of incision is commonly followed by preparing access from the outside of a body to a spine region of interest or respectively the spinous process of a vertebral body of interest.

Commonly, the left and right back muscles (erector spinae) are dissected off the vertebra on both sides and at multiple levels. Performing the method of the first aspect of the invention has the advantageous that the spinous process has only to be detached from the muscles of one body side. This reduces the injury done to the surrounding muscles, which allows for reattachment of the cut off muscles to the spinous process and intact muscle insertion respectively origin, increases the stability of the spine after the surgery and speeds up the recovery of the patients. Therefore one embodiment of the first aspect refers to methods, wherein the one or more muscle origins, respectively muscle insertions are cut off only on the left side or on the right side but not on both sides of the spinous process (respectively the body). Thereby at least one muscle attachment (insertion or origin) of at least one muscle has to be cut off from the spinous process. The origin or insertion of the at least one muscle to be cut off may be selected from the group consisting of multifidus muscles and rotatores muscles (brevi and longi), the muscle splenius capitis, splenius cervicis, semispinalis cervicis (or semispinalis colli), semispinalis thoracis (or semispinalis dorsi), and spinal erectors (Mm. longissimus thoracis, spinalis thoracis, spinalis cervicis, and spinalis capitis).

The erector spinae is not just one muscle, but a group of muscles and tendons that run more or less the length of the spine on the left and the right, from the sacrum or sacral region and hips to the base of the skull. These muscles lie either side of the vertebral column spinous processes and extend throughout the lumbar, thoracic, and cervical regions (lower, middle, and upper back and the neck). The erector spinae is covered in the lumbar and thoracic regions (lower back and lower middle back) by the thoracolumbar fascia, and in the cervical region (neck) by the nuchal ligament. The longissimus muscle is the intermediate and the largest of the three columns. It has three parts with different origin and insertion. Only the longissimus thoracis originates in parts from spinous processes (of the lumbar vertebrae). The spinalis muscle is the smallest and most medial column. It has also three parts wherein the spinalis thoracis originates from the spinous process of L3-T10 and inserts in the spinous process of T8-T2 and the spinalis cervicis originates from the spinous process of T2-C6 and inserts in the spinous process of C4-C2.

Most skeletal muscles are attached to bone on its ends by way of what we call tendons. Nevertheless, the structure that muscles are attached to may be a bone, a tendon or the subcutaneous dermal connective tissue (enthesis). Thereby, enthesis is the connective tissue between tendon or ligament and the bone. As the muscles contract, they exert force on the bones, which help to support and move our body along with its appendages. The insertion and origin of a muscle are the two places where it is anchored, one at each end. In most cases, one end of the muscle is fixed in its position, while the other end moves during contraction. The origin is the attachment site that doesn't move during contraction, while the insertion is the attachment site that does move when the muscle contracts. Alternatively worded, the origin of a muscle is at the bone, typically proximal, which has greater mass and is more stable during a contraction than a muscle's insertion. Depending on the vertebrae to be treated different muscles are attached to the spinous process. The spinous process may include muscle origin as well as muscle insertion. This also varies between different vertebrae. The method of the present invention includes a step including cut off at least one muscle origin or insertion from a spinous process. This means that the surgeon has to cut through at least one structure attaching a muscle to the spinous process. However in case that more than one muscle is attached to the respective spinous process it may be necessary to cut more than one muscle attachment. In general it is possible to cut all muscles attached to the spinous process but it is preferred to cut off only muscles of one body side. Thus one embodiment of the first aspect of the invention relates to a method, wherein the origin or insertion of all muscles originating or inserting on one side of the spinous process are cut off. Therefore the methods of the present invention allows bilateral decompression via unilateral approach.

In general least possible muscles may be cut off. It should be ensured that the following steps of the procedure can be carried out without hindering of muscles. One of these steps is: cutting off the spinous process (osteotomy) at the transition to the lamina arcus vertebrae. Said cut is along or at least approximately along a coronal plane. An alternative wording for that step is therefore: separation of the spinous process from the lamina arcus vertebrae. Subsequently the spinous process and also the muscles still attached to it may be pushed away. The spinous process being cut off the vertebrae may be moved towards the side where no muscle is cut off (or respectively to the body side where all muscles are still attached to the spinous process). Muscles covering the lamina may be carefully pushed away to expose the bony structure. Consequently one embodiment of the first aspect may be a method for the treatment of spinal stenosis including the following steps: incision and preparing access from the outside of a body to a spine region of interest, cutting off at least one muscle origin or insertion from a spinous process, cutting off the spinous process (osteotomy) at the transition to the lamina arcus vertebrae and pushing the spinous process together with the muscles not cut aside, partial resection of the lamina arcus vertebrae and thereby decompression of the spinal cord within the foramen vertebral, osteosynthesis of the spinous process, placing a suture anchor within the spinous process and reattaching the at least one muscle origin or insertion to the spinous process.

After cutting off the spinous process and pushing away the spinous process as well as the muscles attached to it there should be enough space to reach the lamina arcus vertebrae and introduce a tool for cutting bone (e.g. an ultrasound driven blade). Therefore the next step is at least a partial resection of the lamina arcus vertebrae and thereby decompression of the spinal cord within the foramen vertebral. It may be that the partial resection of the lamina arcus vertebrae is sufficient for an adequate decompression. Nevertheless, it may also be that the lamina has to be removed completely. In addition, the surgeon may have to introduce a further tool (or may even use the same as for partial resection) for ablating bone (e.g. degenerative alterations, such as osteophytes) within the foramen vertebral or for removal of spondylophytes narrowing the foramen intervertebral. In general the method according to the first aspect may optionally includes the following step:—removing additional (bone) structures causing a stenosis and a compression of the spinal cord or a spinal nerve. Thereby the structures to be removed may be selected from the group consisting of: bony overgrowth such as osteophytes or spondylophytes (degenerative bony structures at the facet joints and pedicles), hypertrophic ligamentum flavum, hernia of the disc, synovial cysts and spinal tumors.

After decompression the spinous process has to reattached to the lamina. Therefore the inventive methods includes a step of osteosynthesis of the spinous process. This is done using a plate that is adapted to the vertebra to be treated. It fits to the curvature forming the transition between lamina and spinous process. The plate should lie over the cut through the basis of the spinous process. Advantageously, the plate is fixed on each side next to the cut using anchors including a material having thermoplastic properties and are anchored in the bone opening with the aid of vibratory energy used for in situ liquefaction of the material having thermoplastic properties. It is advantageously, that the plate is attached to the bone using a pin or anchor that can be fixed unicortical. This means that the distal layer of dense bone that encloses the spinal cord is not pierced. In addition the length of the pin may be adapted to the length of the bone opening during the in situ liquefaction of the material having thermoplastic properties. Therefore the tip of the pin has to be made of the material having thermoplastic properties so that it melt and that the liquefied material flows into the surrounding spongy parts of the bone. Thus the bone structure is not weakened like it is when using a screw or barbed anchor.

Thereafter the muscles have to be reattached to the spinous process. Therefore, at least one suture anchor is implanted within the spinous process. It is advantageously that the suture anchor is implanted within the area of muscle origin or insertion or at least as near as possible. It may be that more than one suture anchor has to be implanted, e.g. in case that more than one muscle has been detached. One end of the suture should subsequently be threaded through the detached muscle or tissue attaching the muscle to the bone (e.g., a tendon) and the other end should be threaded through the corresponding muscle (the same muscle on the other body side) or tissue attaching the muscle to the bone (e.g., a tendon) which may still being attached to the spinous process. Using the threaded suture ends and if necessary an additional tool (tweezers) the detached muscle or muscles can be pulled up to the spinous process. Thereafter, the ends of the suture may be knotted on the dorsal side of the reattached one. Nevertheless it may also be possible to use a knot-free anchor.

Depending on the muscle cut off the spinous process an additional, optional step may be included. Thereby the muscle that has been detached from the spinous process is sewed up with the same muscle on the other side (preferably not being removed from the spinous process) using an additional suture. Therefore, one to five stiches are made linking both muscles or, respectively, the tissues attaching both muscle to the bone.

It is possible to use a wide range of known anchors and suture anchors within the method of the invention. The anchors as well as the suture anchor should be rather small and holding at least one suture with two open ends. Nevertheless, it is advantageously that the anchor and the at least one suture anchor used within the method of the present invention includes a material having thermoplastic properties. The anchors having thermoplastic properties may be anchored in the bone opening with the aid of vibratory energy used for in situ liquefaction of the material having thermoplastic properties.

Therefore, one embodiment of the first aspect of the invention refers to a method, wherein the suture anchor includes a material having thermoplastic properties and is anchored in the bone opening (of the spinous process) with the aid of vibratory energy used for in situ liquefaction of the material having thermoplastic properties. An additional embodiment relates to a, wherein the osteosynthesis of the spinous process is done using at least two anchors (or pins) including a material having thermoplastic properties and are anchored in the bone opening with the aid of vibratory energy used for in situ liquefaction of the material having thermoplastic properties.

A suture anchor is a small device used during surgical procedures to attach soft tissue, such as ligaments and tendons, to bone. This may be achieved by tying one end of a suture to soft tissue and the other end to a device that "anchors" the suture to the bone. Suture anchors typically are implanted into the bone with at least on suture attached to the anchor. Various techniques of suture attachment have been developed. Most commonly a suture anchor includes an elongate body to which a suture has been attached using an eyelet or the like. Thereby the eyelet—is a hole or a loop in the anchor through which the suture passes. Suture anchors may be made of titanium metal, polyetheretherketone thermoplastic, or biodegradable absorbable material. There are many suture anchors on the market today. In general, they can be classified as screw-in and non-screw-in anchors, commonly using an interference fit or positive generated by barbs. A suture is typically an elongate flexible filament, but may take a variety as different thread or thread-like structures, including imitation fibers, lines, and the like. A suture may be a homogeneous or heterogeneous, and may also include a single filament or a composite suture, such as a two or more twisted or woven filaments. In addition, a suture may be made from a wide array of absorbable (i.e., metabolized by the body) or non-absorbable materials known in the art.

Materials having thermoplastic properties suitable for the suture anchor that can be used in the method according to the invention are thermoplastic polymers, e.g.: resorbable or degradable polymers such as polymers based on lactic and/or glycolic acid (PLA, PLLA, PGA, PLGA etc.) or polyhydroxy alkanoates (PHA), polycaprolactone (PCL), polysaccharides, polydioxanes (PD) polyanhydrides, polypeptides or corresponding copolymers or composite materials containing the named polymers as a component; or non-resorbable or non-degradable polymers such as polyolefines (e.g. polyethylene), polyacrylates, polymetacrylates, polycarbonates, polyamides, polyester, polyurethanes, polysulfones, polyarylketones, polyimides, polyphenylsulfides or liquid crystal polymers LCPs, polyacetales, halogenated polymers, in particular halogenated polyolefines, polyphenylensulfides, polysulfones, polyethers or equivalent copolymers or composite materials containing the named polymers as a component.

One embodiment of the present invention refers to the method for the treatment of spinal stenosis according to the present invention, wherein the at least one anchor is fully made of a bio-degradable material. Another embodiment of the present invention refers to the method for the treatment of spinal stenosis according to the present invention, wherein the osteosynthesis of the spinous process is done using a plate fully made of a bio-degradable material. Specific embodiments of bio-degradable materials are polylactides like LR706 PLDLLA 70/30, R208 PLDLA 50/50, L210S, and PLLA 100% L, all of Böhringer. A list of suitable degradable polymer materials can also be found in: Erich Wintermantel und Suk-Woo Haa, "Medizinaltechnik mit biokompatiblen Materialien und Verfahren", 3. Auflage, Springer, Berlin 2002 (in the following referred to as "Wintermantel"), page 200; for information on PGA and PLA see pages 202 ff., on PCL see page 207, on PHB/PHV copolymers page 206; on polydioxanone PDS page 209. Discussion of a further bioresorbable material can for example be found in C A Bailey et al., J Hand Surg [Br] 2006 Apr.; 31(2):208-12.

Specific embodiments of non-degradable materials are Polyetherketone (PEEK Optima, Grades 450 and 150, Invibio Ltd), Polyetherimide, Polyamide 12, PolyamideII, Polyamide 6, Polyamide 66, Polycarbonate, Polymethylmethacrylate, Polyoxymethylene, or polycarbonate-urethane (e.g. Bionate by DSM, in particular types 65D and 75D). An overview table of polymers and applications is listed in Wintermantel, page 150; specific examples can be found in Wintermantel page 161 ff. (PE, Hostalen Gur 812, Höchst AG), pages 164 ff. (PET) 169 ff. (PA, namely PA 6 and PA 66), 171 ff. (PTFE), 173 ff. (PMMA), 180 (PUR, see table), 186 ff. (PEEK), 189 ff. (PSU), 191 ff (POM-Polyacetal, tradenames Delrin, Tenac, has also been used in endoprostheses by Protec).

The material having thermoplastic properties may further contain foreign phases or compounds serving further functions. In particular, the thermoplastic material may be strengthened by admixed fibers or whiskers (e.g., of calcium phosphate ceramics or glasses) and such represent a composite material. The material having thermoplastic properties may further contain components that expand or dissolve (create pores) in situ (e.g. polyesters, polysaccharides, hydrogels, sodium phosphates), compounds which render the implant opaque and therewith visible for X-ray, or compounds to be released in situ and having a therapeutic effect, e.g., promotion of healing and regeneration (e.g. growth factors, antibiotics, inflammation inhibitors or buffers such as sodium phosphate or calcium carbonate against adverse effects of acidic decomposition). If the thermoplastic material is resorbable, release of such compounds is delayed. If the device is to be anchored not with the aid of vibration energy but with the aid of electromagnetic radiation, the liquefiable material having thermoplastic properties may locally contain compounds (particulate or molecular), which are capable of absorbing such radiation of a specific frequency range (in particular of the visible or infrared frequency range), e.g., calcium phosphates, calcium carbonates, sodium phosphates, titanium oxide, mica, saturated fatty acids, polysaccharides, glucose or mixtures thereof.

Fillers used may include degradable, osseostimulative fillers to be used in degradable polymers, including: β-Tricalciumphosphate (TCP), Hydroxyapatite (HA, <90% crystallinity); or mixtures of TCP, HA, DHCP, Bioglasses (see Wintermantel). Osseo-integration stimulating fillers that are only partially or hardly degradable, for non-degradable polymers include: Bioglasses, Hydroxyapatite (>90% cristallinity), HAPEX®, see SM Rea et al., J Mater Sci Mater Med. 2004 Sep.; 15(9):997-1005; for hydroxyapatite see also L. Fang et al., Biomaterials 2006 Jul.; 27(20):3701-7, and M. Huang et al., J Mater Sci Mater Med 2003 Jul.; 14(7):655-60. Embodiments of bioactive fillers and their discussion can for example be found in X. Huang and X. Miao, J Biomater App. 2007 Apr.; 21(4):351-74), JA Juhasz et al. Biomaterials, 2004 Mar.; 25(6):949-55. Particulate filler types include: coarse type: 5-20 μm (contents, entially 10-25% by volume), sub-micron (nanofillers as from precipitation, preferentially plate like aspect ratio >10, 10-50 nm, contents 0.5 to 5% by volume). Experiments show that liquefaction with the aid of ultrasonic vibration energy allows filling the thermoplastic polymer to a relatively high degree without impairing the capability of the liquefied material to penetrate structures as e.g. the trabecular structure of viable cancellous bone. This fact ensures that anchor loosening is not a problem within the methods of the present invention.

The suture anchor, the pin for fixation of the plate as well as the osteosynthesis plate used in the method according to the invention may consist of any suitable material or material combination (e.g., polymer, metal, ceramic, glass) which material may be bio-resorbable or not bio-resorbable and liquefiable or not liquefiable. Nevertheless, it is advantageously that at least a part (may be the distal part) of the material of the suture anchor is made of a material being liquefiable. Advantageously these materials are not used within the non-bioresorbable or non-biodegradable materials may include surfaces equipped for furthering osseointegration (e.g., per se known surface structures or coatings) where in contact with the bone tissue, in particular if the material of the suture anchor is bio-resorbable or biodegradable and therefore the anchoring function needs to be gradually taken over by osseointegration. Good results have, e.g., been achieved with suture anchors of polylactic acid (PLA) filled with Hydroxyapatite or calciumphosphates, in particular of PLLA filled with 60% tricalciumphosphate or PDLLA 70%/30% (70% L and 30% D/L) filled with 30% biphasic calciumphosphate, combined with suture anchors of PLDLLA 70%/30% (70% L and 30% D/L), as available from Böhringer as LR706. In the case of the suture anchor being integrated in the suture anchor, the two items may consist of the same material, e.g. the above named PLLA filled with 60% tricalciumphosphate or PDLLA 70%/30% (70% L and 30% D/L) filled with 30% biphasic calciumphosphate, wherein the filler content may be smaller in areas in which the material is to be liquefied than in other areas.

If the suture anchor is to be forced into the bone, it needs to include at least in its distal end a material having a corresponding mechanical strength, which is dependent on the mechanical resistance expected of the hard tissue into which the anchor is to be forced. If such resistance is relatively high (forcing through cortical bone or hard and dense cancellous bone) the distal end of the anchor includes e.g. a metal such as, e.g., titanium or a titanium alloy, a ceramic material such as, e.g., sintered calcium phosphate (e.g., hydroxyapatite) or engineering ceramics (e.g., zirkonia, alumina) or PEEK or a comparable high temperature resistant polymer, while other anchor portions are made, e.g., of a biocomposite material such as, e.g., the above mentioned filled polylactides or of one of the other above mentioned thermoplastic polymers. Alternatively such distal end of the anchor may include a hard and possibly abrasive coating, e.g., made by plasma sprayed deposition of calcium phosphate or titanium powder on PEEK or polylactide or biocomposites.

The energy used for the liquefaction of the material having thermoplastic properties is preferably mechanical vibration, in particular ultrasonic vibration generated by a vibration source (e.g., piezoelectric vibration generator possibly including a booster to which the tool is coupled) and the anchoring tool is suitable for transmission of the vibration from its proximal end to its distal face, preferably such that the distal face vibrates with a maximal longitudinal amplitude. For the in situ liquefaction the vibration is transmitted from the distal tool face to the suture anchor and transformed into friction heat in places where the suture anchor is held against a counter element (hard tissue and/or part of the suture anchor). It is possible also to activate the anchoring tool to vibrate in a radial or in a rotational direction.

Alternatively, the energy source may be a laser, preferably emitting laser light in the visible or infrared frequency range and the anchoring tool is equipped for transmitting this light to its distal end, preferably via glass fiber. For the in situ liquefaction the laser light is transmitted into the suture anchor and absorbed where liquefaction is desired, wherein the material of the suture anchor may contain particles or substances effecting such absorption.

The hard outer layer of bones is composed of cortical bone also called compact bone being much denser than cancellous bone. It forms the hard exterior (cortex) of bones. Cancellous bone, also called trabecular or spongy bone, is the internal tissue of the skeletal bone and is an open cell porous network. The vertebrae consist of thin layers of compact bone surrounding a spongy interior. Because of the specific properties of the suture anchor and the pins they require little space. It is possible to anchor them in the vertebrae in a way that only one cortex is used but enough strength is provided for the function of the suture. Thus, the present invention refers to methods wherein the suture anchor and/or the anchor used during osteosynthesis are implanted unicortical. Thereby unicortical means that the suture anchor or pin is anchored in a blind hole. Thus, the bone opening for the anchor goes only through one thin layer of the compact bone surrounding the vertebrae. In addition, also the material of the suture anchor after liquefaction and resolidification does not invade the second cortex or layer of compact bone. This ensures that the spinal cord is not hurt. Similar, this is also true for pins implanted in the direction towards the lateral foramina. In this case, the risk of injury of the spinal nerve is minimized.

The suture anchor used is advantageously designed in a way that it can be implanted using a bone opening being shorter than the suture anchor, which makes it possible to set a suture anchor within the tip of a small spinous process. Therefore at least a part of the suture anchor, its pin-like structure or the pin should be made fully of liquefiable material. It is advantageously that at least one section of the suture anchor located within its length and including the full cross section of the suture anchor is made of a thermoplastic material to be liquefied. Using such a suture anchor makes it possible to have a short bone opening because the liquefiable material of the suture anchor invades in the surrounding spongy bone tissue. Therefore during implantation the length of the suture anchor shortens but the material of the anchor is distributed within the area surrounding the bone opening. By the same the pulling force to be exerted on the suture increases. The same applies respectively to the pin to be used for osteosynthesis of the spinous process.

In case that the surgeon prefers to detach the muscles on both sides of the spinous process it may not be necessary to cut the spinous process. When using the suture anchors as described above it is even possible to set two anchors at the dorsal tip of the spinous process to reattach the muscles. Because the suture anchors can be adapted to a bone opening shorter that the anchor itself and because the anchors do not weaken the structure of the bone but even make it denser because of the material invading in the spongy structures. Thus it is possible to use two anchors which intersect. Therefore two anchors may be located within minimum space such as the spinous process.

Consequently, one embodiment refers to a method for the treatment of spinal stenosis including:

cutting off a muscle origin or insertion from (each side of) a spinous process resecting at least a part of the lamina arcus vertebrae and thereby decompression of the spinal cord within the foramen vertebral placing two suture anchors within the spinous process and reattaching the muscle origin or insertion to the spinous process, wherein one suture anchor is located on each side of the spinous process.

Inserting at least one suture anchor into a bone opening and anchoring the at least one suture anchor may include the following steps: Introducing the suture anchor into the bone opening with the suture having two freely accessible ends by pushing the suture anchor into the bone opening using a tool and by simultaneously or later transmitting energy via the tool to the suture anchor thereby liquefying material of the suture anchor having thermoplastic properties. Using the inventive method there is no need to pull the anchor tight to determine whether full insertion has been reached.

The goal of the method for surgical treatment as described so far is to alleviate neural compression (decompression). In selected patients with a deformity or instability, it is necessary to stabilize further the spine (fusion), so as to prevent further spinal compression and recurrent symptoms. Therefore it may be that in addition to the laminectomy, a spine fusion surgery is also necessary in order to achieve adequate decompression. This is especially true if the nerve root of a spinal nerve is compressed as it leaves the spine, known as foraminal stenosis. The second aspect refers to methods of for spine stabilization. Thereby suture anchors are used to implement a tension band wiring. The goal is to stabilize two articulating vertebrae or to adjust the curvature of the spine formed by these vertebras. Thus, spondylolisthesis (forward displacement) of a vertebra or retrolisthesis (posterior displacement) of a vertebra with respect to the adjacent vertebra should be avoided. Thereby the adjacent vertebra is mostly the uppermost vertebra of spinal fusion. The methods of the second aspect are helpful in connection with spine decompression respectively after laminotomy or laminectomy or in connection with a spinal fusion. The main objective of the methods according to the second aspect is to build a transition zone to bridge a fused segment to a nonfused segment by spreading the forces.

This needs to be carefully differentiated from rigid fixation of the spine, where a fusion is intended. Spinal fusion, also called spondylodesis or spondylosyndesis, is thereby defined as neurosurgical or orthopedic surgical technique that joins two or more vertebrae into one single structure. Spinal fusion prevents any movement between the fused vertebrae. A soft stabilization or flexible stabilization, as described herein leaves the spinal segment mobile, and its intention is to alter the load bearing pattern of the motion segment, as well as to control any abnormal motion at the segment. The control of abnormal motions and more physiological load transmission should relieve pain, and prevent adjacent segment degeneration. A remote expectation is that, once normal motion and load transmission is achieved, the damaged disc may repair itself, unless of course the degeneration is too advanced.

There is the need for a posterior soft stabilization system promising to add stability after decompressive laminectomy, spinal fusion or facetectomy. Therefore the second aspect of the present invention describes a new method for introducing a tension-band wire for stabilization of the spine besides the spinous processes. It consists of at least four suture anchors as described above that can be placed in the lamina arcus vertebrae.

One embodiment of the second aspect refers to a method for spine stabilization including the following steps: positioning of at least one suture anchor per lamina arcus vertebrae of at least two adjacent vertebrae and knotting together the suture ends of two anchors located in different vertebras at corresponding locations within the lamina arcus vertebrae.

It is also possible to fixate the suture anchors in the spinous process, one on each side. In the cervical spine it can be sufficient to use only one suture anchor per vertebrae and fix it at the dorsal end of the spinous process. Another location of the suture anchors may be the processus transversus vertebrae. In case that the tension wiring is used to prevent a scoliotic instability it is even advantageously to induce the suture anchors only on one side within the processus transversus vertebrae.

Therefore another embodiment of the invention refers to a method for spine stabilization including the following steps: positioning of at least one suture anchor per vertebrae of at least two adjacent vertebrae and knotting together the suture ends of two anchors located in different vertebras at corresponding locations within the lamina arcus vertebrae, wherein the suture anchor is implanted within the lamina arcus vertebrae, the spinous process or the processus transversus vertebrae. A preferred embodiment of the invention refers to a method for spine stabilization including the following steps: positioning of at least two suture anchor per vertebrae of at least two adjacent vertebrae and knotting together the suture ends of two anchors located in different vertebras at corresponding locations within the lamina arcus vertebrae, wherein the suture anchor is implanted within the lamina arcus vertebrae, the spinous process or the processus transversus vertebrae.

For positioning of a suture anchor per lamina arcus vertebrae of at least two adjacent vertebrae (and at least four anchors in total) the surgeon has to drill bone openings into the lamina arcus vertebrae. In the end both lamina arcus vertebrae of all vertebrae to be stabilized should have at least one bone opening. These openings can be blind holes. It is advantageously that the bone openings do not have to reach the ventral cortex (or layer of dense bone). Within these bone openings a suture anchor has to be implanted.

It is also possible to use two suture anchors per lamina arcus vertebrae. Within the thoracic and lumbar spine this is even advantageously. For positioning of two suture anchor per lamina arcus vertebrae of at least two adjacent vertebrae (and at least eight anchors in total) the surgeon has to drill two adjacent bone openings into the lamina arcus vertebrae. In the end both lamina arcus vertebrae of all vertebrae to be stabilized should have two bone openings. These openings can be blind holes. It is advantageously that the bone openings do not have to reach the ventral cortex (or layer of dense bone). Within these bone openings a suture anchor has to be implanted.

It is possible to use a wide range of known suture anchors within the method of the second aspect of the invention. The suture anchor should be rather small and holding at least one suture with two open ends. Nevertheless, it is advantageously the at least one suture anchor used within the method of the present invention includes a material having thermoplastic properties. The suture anchor having thermoplastic properties may be anchored in the bone opening with the aid of vibratory energy used for in situ liquefaction of the material having thermoplastic properties. It is advantageously to use the same anchors as described for the first aspect of the present invention. Therefore all statements done before in respect to the anchors are also true in regard to the second aspect.

In particular, one embodiment of the second aspect refers to the method for spine stabilization according to the present invention, wherein the anchors are fully made of a biodegradable material. In addition, one embodiment relates to the method according to the second aspect, wherein the suture anchors are implanted only unicortical.

In the second step of the method according to the second aspect the suture ends of two anchors are knotted together. Therefore one suture end of the first anchor is knotted with a suture end of a second anchor and the second suture end of the first anchor is knotted with the second suture end of the second suture anchor. It is advantageously to do this in a way that two parallel sutures run from one anchor on the first vertebrae to another anchor implanted within the adjacent vertebrae. In this case the sutures should also run approximately parallel to the spine. The sutures may also run diagonally (crisscross). It is preferred that the sutures of two anchors are knotted, wherein the anchors are located at approximately the same position within adjacent vertebrae. Thereby the sutures should be tensioned. Thereby the tension can be adapted individually, also individually per side in a way that scoliotic tendencies can be compensated.

The suture of the used suture anchor may be made of any commonly used material. Suitable are, e.g., nylon, polyester, PVDF and polypropylene. The sutures must be strong enough to hold the force on the vertebrae securely but flexible enough to be knotted and they must be hypoallergenic. It is preferred to use a flexible suture (e.g. DYNACORD® made of two outer sheaths of braided fibers and a core of silicone and salt). Then advantage of these flexible suture is that they respond to changes in tension that occur over time to promote stability. In particular the combination with the suture anchors to be fixed using vibration is advantageously, because these anchors fixed by form closure show no creep tendency.

A posterior soft stabilization system introduced according to a method of the second aspect promises to add stability to the area of spine above fused vertebrae. Therefore one embodiment of the second aspect refers to a method, wherein the lower of the adjacent vertebrae to be stabilized is joined to the vertebrae further down by spinal fusion method. This is in particular important within the thoracic or lumbar spine. In connection with the cervical spine, the method is rather important in combination with laminotomy or laminectomy. This means the suture anchors introduced according to a method of the second aspect are used to stabilize vertebrae after laminotomy or laminectomy or to adjust a defined lordosis. It may be the aim of the method to induce a defined kyphosis resp. lordosis or to prevent a progressive, further kyphosis by a rotation or the spondylolisthesis. Therefore the method of the invention aims for stabilization (in the medium to long term) stabilization by achieving the formation of ligament-like structures or shortening of ligaments. Therefore the sutures may supported by graft tissue, such as allografts (like dermograft), autografts or even textile patches.

Spinal fusion is commonly performed together with rigid instrumentation to treat various lumbar spine disorders. Current methods of fixation include posterior pedicle screw instrumentation with posterior lumbar interbody fusion (PLIF) or transforaminal lumbar interbody fusion (TLIF), posterior pedicle screw instrumentation with anterior lumbar interbody fusion (ALIF), and anterior plate and screw instrumentation with ALIF. Over the past 20 years, PLIF with pedicle screw instrumentation has gained popularity in the spine community, and may therefore be considered a standard for fusion to which alternative treatment methods can be compared. Consequently, the second aspect of the present invention refers to methods, wherein the fusion is supplemented with hardware (screws, plates, rods).

The methods of the second aspect may further be useful to create or recreate a posterior tension band. The 'posterior tension band' is part of the spine's anatomy found at the back of the spine (posterior). Elements that make up the posterior tension band are the spinous processes and lamina (bony plate that is part of each vertebral body) along with the ligaments that join these. Often, these posterior elements are removed during a spinal decompression procedure, which can potentially destabilize the spine. Dynamic stabilization restores the posterior tension band (posterior support) without the need for spinal fusion. Therefore one embodiment refers to a method, wherein the knotted sutures are augmented using an artificial ligament such as a tissue graft which may be attached to the suture.

The methods according to the second aspect of the invention results in dynamic stabilization of the spine. The resulting system of sutures and optionally artificial ligaments may be defined as a system, which would favorably alter the movement and load transmission of a spinal motion segment, without the intention of fusion of the segment.

DESCRIPTION OF THE PREFERRED EMBODIMENTS

The following more detailed description of the embodiments of the method is a representative of exemplary embodiments of the technology, wherein similar parts are designated by same numerals throughout. Standard medical planes of reference and descriptive terminology are employed in this specification. A sagittal plane divides a body into right and left portions. A transverse plane divides a body into superior and inferior portions. Anterior means toward the front of the body. Posterior means toward the back of the body. Superior means toward the head. Inferior means toward the feet. Medial means toward the midline of the body. Lateral means away from the midline of the body. Axial means toward a central axis of the body. Proximal means toward the trunk, or, in the case of an inanimate object, toward a user. Distal means away from the trunk, or, in the case of an inanimate object, away from a user. Dorsal means toward the top of the foot. Plantar means toward the sole of the foot. Ipsilateral means on the same side of the body. Contralateral means on the opposite side of the body.

Figure 1:
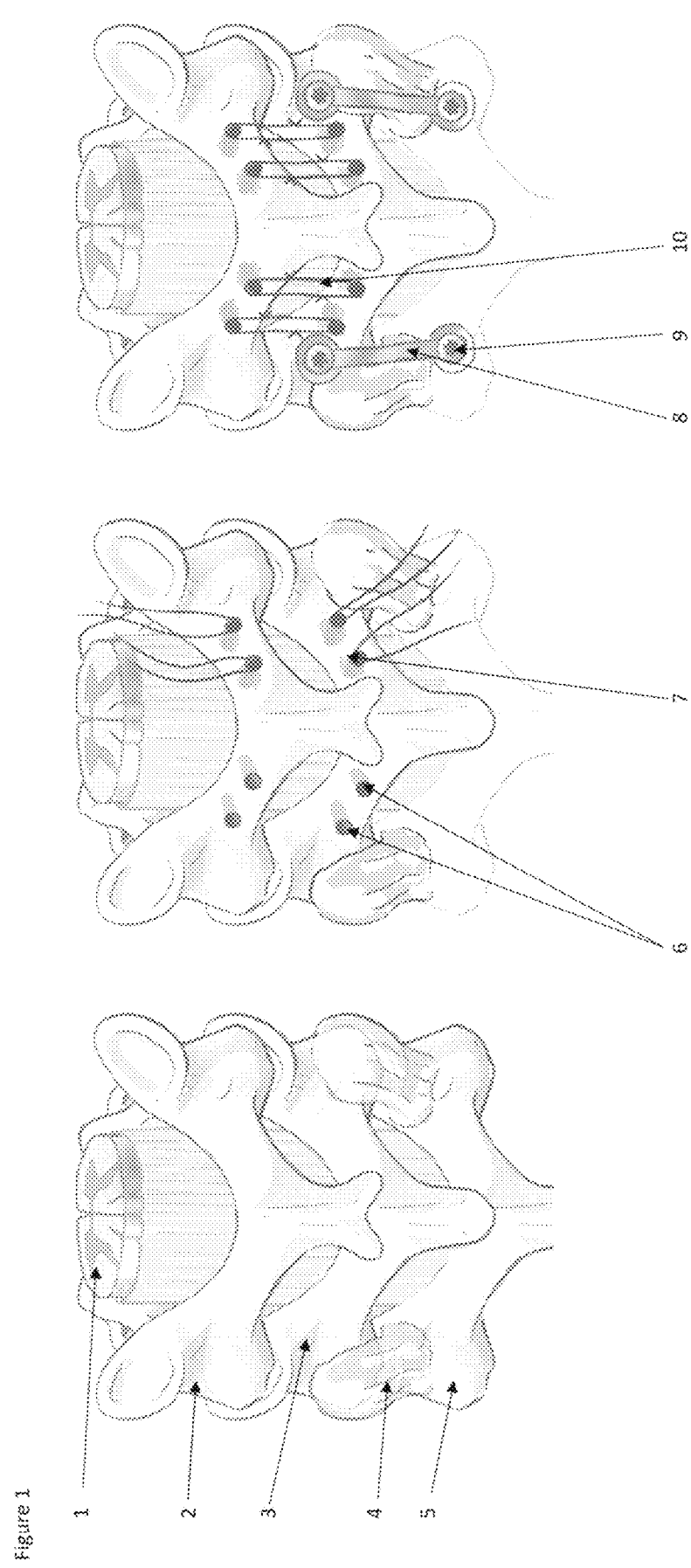
FIG. 1 shows a schematic overview of the method according to aspect 2 according to the present invention.

FIG. 1 illustrates the method according to aspect 2 of the present invention. Exemplarily, the method is shown at the cervical spine. The figure shows a fusion of the first thoracic vertebra 5 with vertebra prominens 3, the seventh cervical vertebra, which are shown with the spinal cord 1 and the articular capsule 4. Therefore pedicle screws 9 together with a fusion rod 8 are used. The articulation between the seventh cervical vertebra 3 and the sixth cervical vertebra 2 is stabilized by a tension band wiring according to the second aspect of the invention. In a first step two bone openings 6 are made in each lamina arcus vertebrae of each vertebrae, therefore in total eight bone openings 6 are introduced. These openings do not have to be through holes. It is sufficient that only the proximal cortex of the lamina is opened up by drilling. It is shown in FIG. 1 that the bone openings are made before the fusion is established but this is not necessary, the openings may also be drilled after the fusion is established. Subsequently in each bone opening a suture anchor is fixed 7. Thereby it is important that the anchors used can be fixated unicortical. The anchors may be fixed by liquefying a thermoplastic material of the anchors using oscillation. The liquefied material is displaced into the pores of the surrounding bone. Therefore, the bone opening can be shorter than the anchor. During fixation the anchor shortens depending on the amount of thermoplastic material liquefied. Therefore, the user may adapt the length of the anchor after implantation to the individual vertebrae and circumstances. The anchor has enough strength for the bracing also in case that it is fixed only in an opening of minimal length (1.5-3 mm). It is suitable to use very small anchors such as the SportWelding® Fiji Anchor®.

Figure 3:
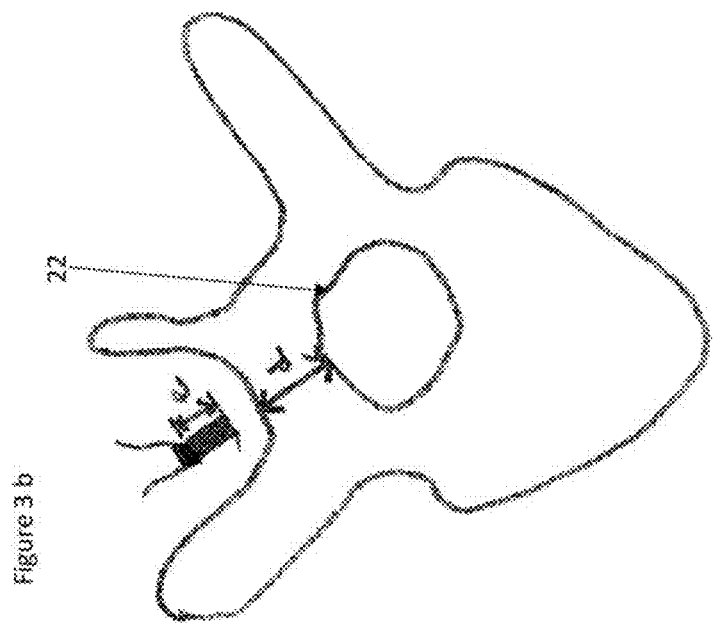
FIG. 3 shows a schematic view of a thoracic vertebrae having openings with and without suture anchors for the method according to aspect 2 of the present invention.
Figure 3:
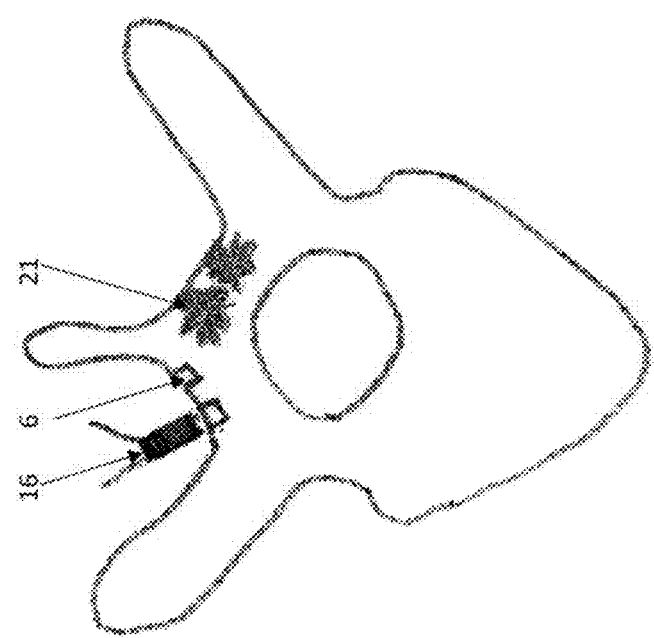

FIG. 3 shows a schematic view of the sixth thoracic vertebrae cut in transverse plane. In the vertebrae shown in FIG. 3a) the lamina arcus vertebrae on the left side has two bone openings 6. Furthermore a suture anchor 16 before implantation is shown. The lamina arcus vertebrae on the left side shows two anchors after fixation (not shown are the sutures of these anchors). One can see that the liquefied material 21 of the anchors has been filled the pores of the cancellous bone within the lamina arcus vertebrae. This ensures the strength of the anchoring. The width d of the lamina arcus vertebrae as shown in FIG. 3b may be smaller than the length e of the anchor (d<e). In particular d may be between 4 to 5 mm and e around 7 mm. The opening used to implant the anchor is preferably even less than the width d. Therefore the method of the present invention is able to protect the spinal cord because the distal cortical end of the lamina arcus vertebrae 22 stays intact (the bone openings 6 are no blind holes). This enables to treat also fragile vertebrae or vertebrae with small laminas (cervical spine) using the method of the present invention.

In the last step the bracing is finalized by knotting the sutures 10. Therefore the suture ends of two anchors being located in opposite openings on neighboring vertebrae are linked by two knots. This results in two double stranded links for each lamina arcus vertebrae. The strands or knotted sutures 7 of one pair of anchors run essentially parallel to each other.

Figure 2:
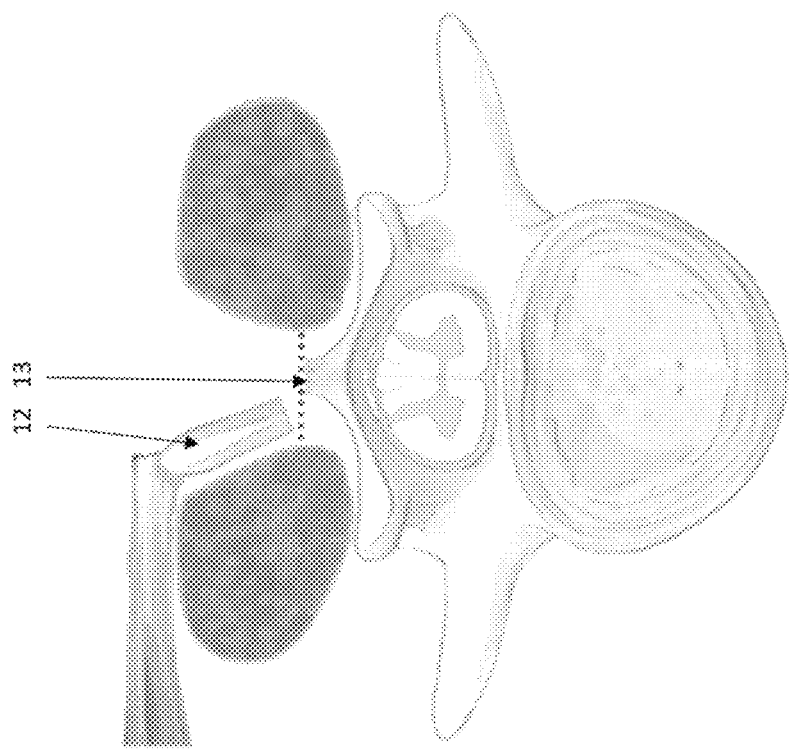
FIG. 2 shows a schematic overview of the method according to aspect 1 of the present invention.
Figure 2:
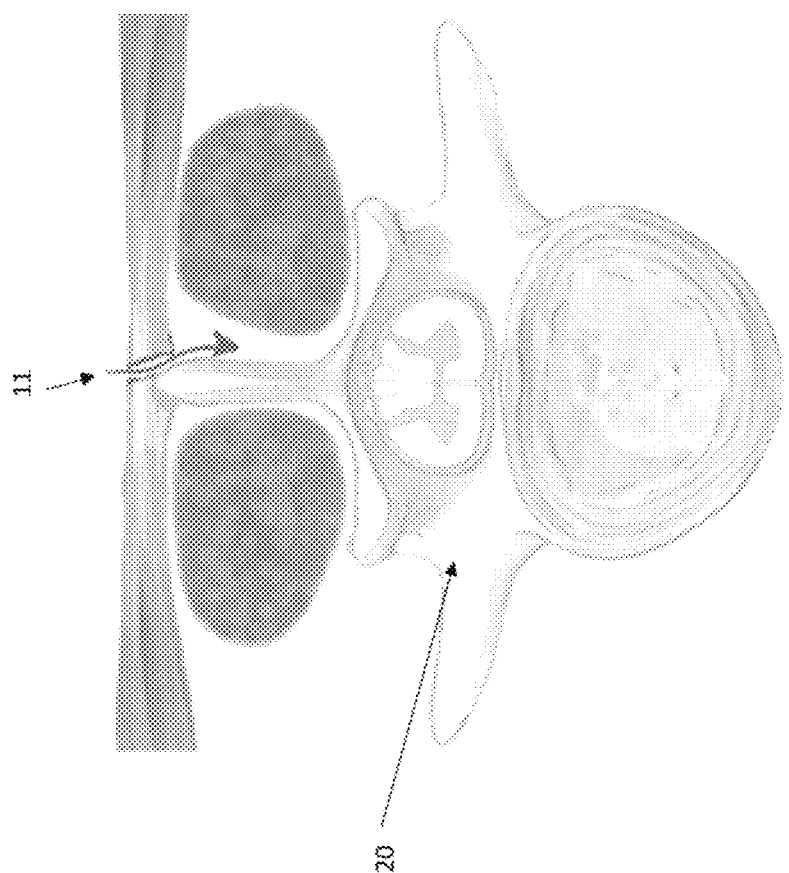
Figure 2:
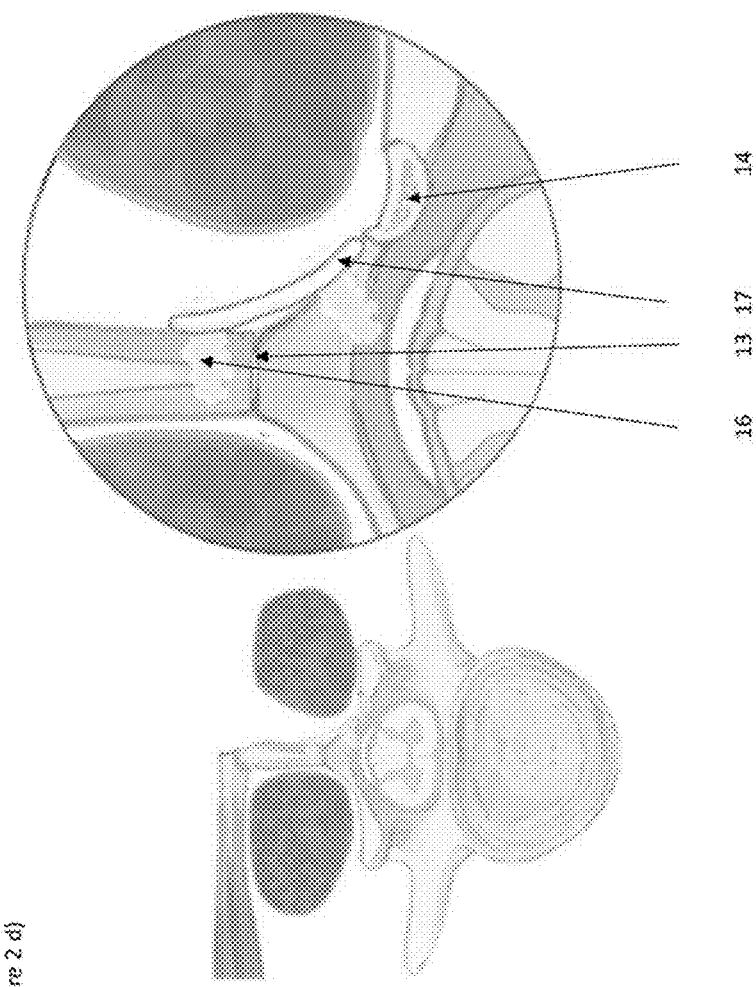
Figure 2:
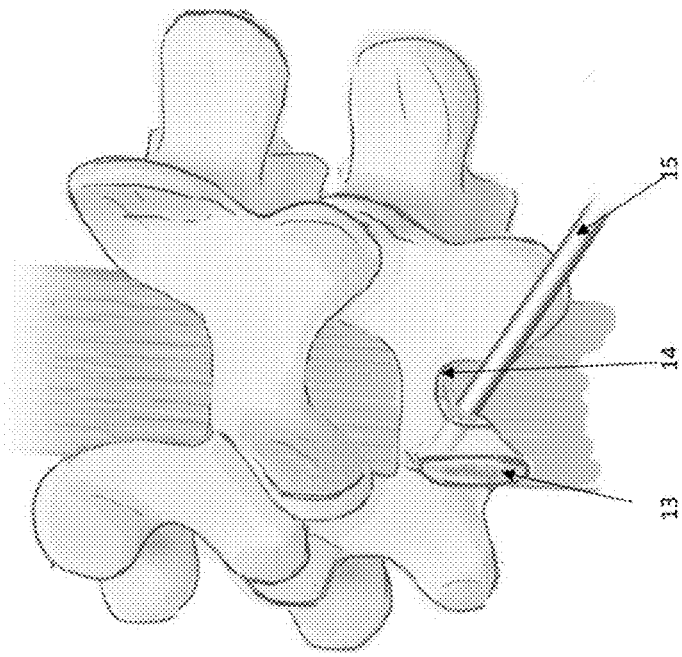
Figure 2:
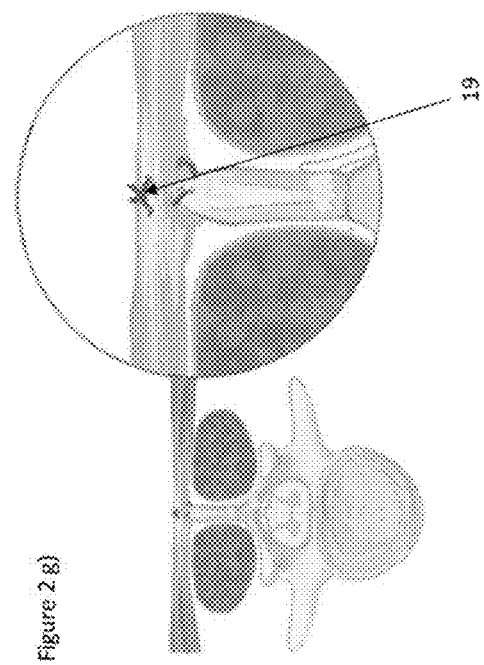
Figure 2:
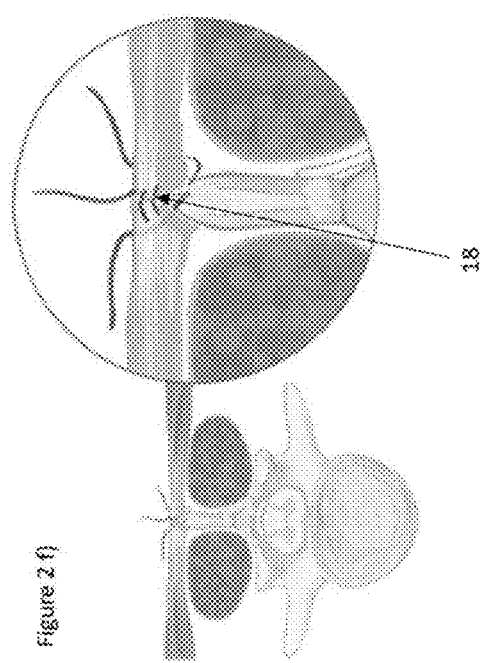
Figure 2:
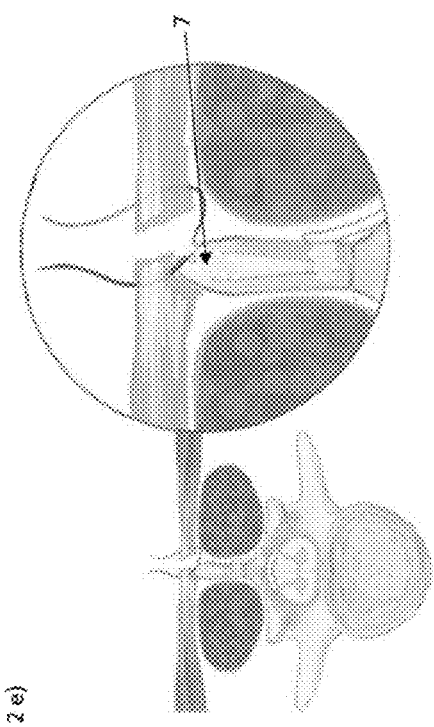

FIG. 2 illustrates the method according to aspect 1 of the present invention. The method refers to a method of laminotomy or laminectomy. Shown is exemplarily a lumbar vertebrae 20. In a first step the muscle insertion or the muscle origin 11 (depends on the vertebrae to be treated) of the autochthonous back muscles at the spinous process 12 are cut. It may be that only one origin or respectively insertion has to be cut to get enough space to reach the basis of spinous process and the area of the lamina arcus to be treated. Deepening on the vertebrae it may also be that more than one muscle inserts or origins 11 at the respectively spinous process 12 and has to be cut. In FIG. 2a) is shown that the origin of the longissimus has to be cut. The cut should be as close to the bony structure as possible. The method according to the invention has the advantage that only the muscle insertion/origin of one side has to be cut. Thereafter (FIG. 2b) the muscles filling up the groove on the side of the spinous processes of the vertebrae (here the multifidus muscle consisting of a number of fleshy and tendinous fasciculi) can be pushed so that it is possible to cut away the spinous process 12 at its basis or transition to the lamina arcus vertebrae. The cut 13 at a frontal or coronal plane of the vertebrae separates the spinous process from the vertebrae. The cut 13 allows to pushes away the spinous process 12 together with the muscles attached thereto. In the subsequent step (FIG. 2c) a partial resection 14 of the lamina arcus vertebrae is carried out. This partial resection may be enough to result in the wanted decompression of the spinal cord. Nevertheless, it may be necessary to introduce a tool 15 that allows to ablate degenerative alterations, such as osteophytes, within the foramen vertebral (decompression of the spinal cord) or the foramen intervertebral (decompression of the spinal nerves and arteria vertebral).

Thereafter (step shown in FIG. 2d) the spinous process may be relocated and fixed to the vertebrae. It is preferred to use a plate 17 made of biodegradable absorbable material which is fixed using two pins or anchors 16 made of thermoplastic material. These pins 16 can be liquefied using oscillation. As described for the anchors above the liquefied material invades in the porous structures of the cancellous bone and thus anchors the plate. The plate has to be fixed to traverse the cut 13 of the spinous process but does not need to reach the partial resection of the lamina arcus vertebrae.

In the following step at least one suture anchor 7 has to be placed within the spinous process. It may be that more than one anchor is necessary or at least suitable e.g. in case that more than one muscle insertion or origin has been cut on the respective side of the spinous process. It is preferred that the anchor is set in a way that it is within the area of the muscle origin or insertion of the muscle to be fixed. In this case the muscle can be fixed directly to the bone which is infringed by the opening which is a suitable stimulus for recruitment of reparative cells and genes. Therefore, it is helpful for the reattachment of the muscle that the anchor is placed directly within the area of muscle insertion or origin. This should be possible also for narrow spaces because the anchors are short and can be set within a bone opening being even shorter, see FIG. 3.

One end of the suture of the suture anchor 7 is threaded through the muscle insertion or origin not cut off from the spinous process and the second end of the suture is threaded through the tendon or of the muscle or the muscle itself which has been cut off from the spinous process. With the help of the suture ends the muscle that has been cut can be pulled back to the spinous process and can be attached to the spinous process and the corresponding muscle on the other side of the spinous process. Finally the ends of the suture are knotted as shown in FIG. 2g). The knot 19 of the suture is located on the tendinous insertion or origin of the muscle respectively on the dorsal side of the muscle.

FIG. 2f) shows an optional step of the method. In addition, to the reattachment of the muscle to the bone and the corresponding muscle of the other side using the suture of the suture anchor 7 it may be suitable to use an additional suture 18 reattach the muscle to the corresponding muscle of the other body side. This is done by simple stitching to sew the muscle being cut off to the corresponding muscle which stayed on the spinous process.

What is claimed:

1. A method for the treatment of spinal stenosis comprising:
    cutting off a muscle origin or insertion from a spinous process;
    cutting off the spinous process at the transition from the spinous process to the lamina arcus vertebrae resulting in two entirely separated parts of the vertebra, wherein a first part of the two entirely separated parts being the spinous process and a second part of the two entirely separated parts being the remaining vertebra which encloses the spinal cord completely;
    resecting at least a part of the lamina arcus vertebrae and thereby decompressing the spinal cord within the foramen vertebral;
    performing osteosynthesis of the spinous process; and
    placing a suture anchor within the spinous process and reattaching the muscle origin or insertion to the spinous process;
    wherein muscle origins or insertions are cut off only on the left side or on the right side but not on both sides of the spinous process.

2. The method according to claim 1, wherein the suture anchor comprises a material having thermoplastic properties and is anchored in a bone opening with aid of vibratory energy used for in situ liquefaction of the material having thermoplastic properties.

3. The method according to claim 1, wherein the osteosynthesis of the spinous process is done using at least two anchors comprising a material having thermoplastic properties and wherein the anchors are each anchored in a respective bone opening with aid of vibratory energy used for in situ liquefaction of the material having thermoplastic properties.

4. The method according to claim 1, wherein the osteosynthesis of the spinous process is done using a plate fully made of a bio-degradable material.

5. The method according to claim 1, wherein the spinal stenosis is a cervical spinal canal stenosis, thoracic spinal canal stenosis, lumbar spinal canal stenosis or wide spinal canal stenosis.

6. The method according to claim 1, wherein the origin or insertion of all muscles originating or inserting on one side of the spinous process are cut off.

7. The method according to claim 1, wherein the origin or insertion of at least one muscle selected from the group consisting of multifidi and rotatores, splenius capitis, splenius cervicis, semispinalis cervicis, semispinalis thoracis, and spinal erectors is cut off.

8. The method according to claim 1, wherein the suture anchor and an anchor used during osteosynthesis are implanted unicortical.

9. A method for spine stabilization comprising:
    positioning one suture anchor per lamina arcus vertebra of at least two immediately adjacent articulating vertebrae, wherein each suture anchor holds at least one suture with two open ends; and
    knotting together the open ends of the sutures in a way that two parallel sutures run from a suture anchor on a first vertebra of the at least two immediately adjacent articulating vertebrae to another suture anchor implanted within a second vertebra of the at least two immediately adjacent articulating vertebrae at corresponding locations within the lamina arcus vertebra;
    wherein:
        a lower one of the at least two immediately adjacent articulating vertebrae is an uppermost vertebra of a spinal fusion joining two or more vertebrae, wherein the spinal fusion uses rigid instrumentation and prevents any movement between the joined vertebrae, or
        the at least two immediately adjacent articulating vertebrae are not part of a spinal fusion.

10. The method according to claim 9, wherein the suture anchors comprise a material having thermoplastic properties and wherein the suture anchors are each anchored in a respective bone opening with aid of vibratory energy used for in situ liquefaction of the material having thermoplastic properties.

11. The method according to claim 9, wherein the suture anchors are implanted only unicortical.

12. The method according to claim 9, wherein the knotted sutures are augmented using an artificial ligament.

* * * * *